(12) United States Patent
Mori et al.

(10) Patent No.: US 7,009,706 B2
(45) Date of Patent: Mar. 7, 2006

(54) MEASURING CHIP

(75) Inventors: Nobufumi Mori, Kaisei-machi (JP);
Takeharu Tani, Kaisei-machi (JP);
Atsushi Mukai, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 10/318,406

(22) Filed: Dec. 13, 2002

(65) Prior Publication Data

US 2003/0184755 A1 Oct. 2, 2003

(30) Foreign Application Priority Data

Dec. 14, 2001 (JP) ............................. 2001-381658
Oct. 15, 2002 (JP) ............................. 2002-299922

(51) Int. Cl.
*G01N 21/55* (2006.01)

(52) U.S. Cl. ..................................... 356/445
(58) Field of Classification Search ............... 356/445, 356/246

See application file for complete search history.

(56) References Cited

U.S. PATENT DOCUMENTS

| 5,936,126 A | 8/1999 | Ruhl et al. |
| 6,597,456 B1 * | 7/2003 | Kubo et al. .................. 356/445 |
| 2001/0040680 A1 | 11/2001 | Kubo et al. |

FOREIGN PATENT DOCUMENTS

| EP | 0 577 285 A1 | 1/1994 |
| JP | 6-167443 | 6/1994 |

OTHER PUBLICATIONS

G.M. Yang, G.M. Sessler and W.Hatke; Electret Properties of Cycloolefin-Copolymer-Polypropylene Blends; ELECTRETS, 1999, ISE 10, Proceedings, 10th International Symposium on Athens, Greece 22-24 Sep. 22, 1999, pp. 317-320.

Lyon L A et al.; "Surface plasmon resonance of colloidal Au-modified gold films"; Sensors and Actuators B, Elsevier Sequoia S.A., Lausanne, CH, vol. 54, No. 1-2; Jan. 25, 1999; pp. 118-124.

Netti M C et al.; "Confined Surface Plasmons in Gold Photonic Nanocavities"; Advanced Materials, VCH Verlagsgesellschaft, Weinheim, DE, vol. 13, No. 19; Sep. 14, 2002; pp. 1368-1370.

Database WPI Section Ch, Week 198922; Derwent Publications Ltd., London GB; AN 1989-160908 & XP002234755 & & JP 01 10252 A (Kurray Co Ltd), Apr. 20, 1989.

Database WPI Section Ch, Week 199208; Derwent Publications Ltd., London GB; AN 1992-060111 XP002234756 & JP 04 004000 A (Idemitsu Kosan Co Ltd), Jan. 8, 1992.

(Continued)

*Primary Examiner*—Gregory J. Toatley, Jr.
*Assistant Examiner*—Amanda Merlino
(74) *Attorney, Agent, or Firm*—Sughrue Mion, PLLC (57) ABSTRACT

A measuring chip comprising a dielectric block and a thin film layer formed on one surface of the dielectric block. The thin film layer is used for placing a sample thereon. The dielectric block is formed as a single block, which includes an entrance surface at which a light beam enters the dielectric block, an exit surface from which the light beam emerges, and the one surface on which the thin film layer is formed. In addition, the dielectric block is integrated with the thin film layer and formed from a resin whose photoelastic coefficient is less than $50 \times 10^{-12}$ $Pa^{-1}$.

6 Claims, 8 Drawing Sheets

OTHER PUBLICATIONS

Database WPI Section Ch, Week 198827; Derwent Publications Ltd., London GB; AN 1988-186196 XP002234757 & JP 63 122749 A (Idemitsu Petrochem Co), May 26, 1988.
Database Inspec 'Online! Institute of Electrical Engineers, Stevenage, GB; Natsuume et al: "A new high heat resistant, high clarity, and high humidity resistant polymer for optical uses" Database accession No. 3811266 XP002234754 & Materials for Magneto-Optic Data Storage Symposium, San Diego, CA, USA, Apr. 25-26, 1989, pp. 245-250, 1989, Pittsburgh, PA, USA, Mater, Res. Soc. USA.
Database WPI Section Ch, Week 199433; Derwent Publications Ltd., London GB; AN 1994-269592 XP002234758 & JP 06 200113 A (Nippon Zeon KK), Jul. 19, 1994.
"Spectral Research" vol. 47, No. 1, 1998, 21-23, 26-27, Surface Retracto—Sensor Using Evanescent Waves : Principles and Instrumentation.

* cited by examiner

MEASURING CHIP

BACKGROUND OF THE INVENTION

1. Field of the Invention

The present invention relates to a measuring chip that is employed in a surface plasmon resonance measurement apparatus for quantitatively analyzing the properties of a substance in a liquid sample by utilizing surface plasmon excitation.

2. Description of the Related Art

If free electrons vibrate collectively in a metal, a compression wave called a plasma wave will be generated. The compression wave, generated in the metal surface and quantized, is called a surface plasmon.

There are various kinds of surface plasmon resonance measurement apparatuses for quantitatively analyzing a substance in a liquid sample by taking advantage of a phenomenon that the surface plasmon is excited by a light wave. Among such apparatuses, one employing the "Kretschmann configuration" is particularly well known (e.g., see Japanese Unexamined Patent Publication No. 6(1994)-167443).

The surface plasmon resonance measurement apparatus employing the aforementioned "Kretschmann configuration" includes (1) a dielectric block formed into the shape of a prism; (2) a metal film, formed on a surface of the dielectric block, for placing a sample thereon; (3) a light source for emitting a light beam; (4) an optical system for making the light beam enter the dielectric block so that a condition for total internal reflection is satisfied at the interface between the dielectric block and the metal film and that various angles of incidence, including a surface plasmon resonance condition, are obtained; and (5) photodetection means for measuring the intensity of the light beam totally reflected from the interface to detect surface plasmon resonance (SPR).

In order to obtain various angles of incidence in the aforementioned manner, a relatively thin light beam may be deflected to strike the above-mentioned interface, or relatively thick convergent or divergent rays may strike the interface so that they have components which are incident at various angles. In the former, a light beam whose reflection angle varies with the deflection thereof can be detected by a small photodetector that is moved in synchronization with the deflection, or by an area sensor extending in the direction where the angle of reflection varies. In the latter, on the other hand, rays reflected at various angles can be detected by an area sensor extending in a direction where all the reflected rays can be received.

In the above-described surface plasmon resonance measurement apparatus, if a light beam strikes the thin film layer at a specific incidence angle $\theta_{sp}$ greater than a critical incidence angle at which total internal reflection (TIR) takes place, an evanescent wave having electric field distribution is generated in a liquid sample in contact with the thin film layer. The evanescent wave excites the above-described surface plasmon at the interface between the thin film layer and the liquid sample. When the wave vector of the evanescent wave is equal to the wave number of the surface plasmon and therefore the wave numbers between the two are matched, the evanescent wave resonates with the surface plasmon and the light energy is transferred to the surface plasmon, whereby the intensity of the light totally reflected from the interface between the dielectric block and the metal film drops sharply. This sharp intensity drop is generally detected as a dark line by the above-described photodetection means.

Note that the aforementioned resonance occurs only when an incident light beam is a p-polarized light beam. Therefore, in order to make the resonance occur, it is necessary to make settings in advance so that a light beam can strike the aforementioned interface as a p-polarized light beam.

If the wave number of the surface plasmon is found from a specific incidence angle $\theta_{sp}$ at which attenuated total reflection (hereinafter referred to as ATR) takes place, the dielectric constant of a sample to be analyzed can be calculated by the following Equation:

$$K_{sp}(\omega) = \frac{\omega}{c} \sqrt{\frac{\varepsilon_m(\omega)\varepsilon_s}{\varepsilon_m(\omega) + \varepsilon_s}} \qquad (1)$$

where $K_{sp}$ represents the wave number of the surface plasmon, $\omega$ represents the angular frequency of the surface plasmon, c represents the speed of light in vacuum, and $\epsilon_m$ and $\epsilon_s$ represent the dielectric constants of the metal and the sample, respectively.

If the dielectric constant $\epsilon_s$ of the sample is found, the concentration of a specific substance in the sample is found based on a predetermined calibration curve, etc. As a result, the specific substance can be quantitatively analyzed by finding the specific incidence angle $\theta_{sp}$ at which the intensity of reflected light drops sharply.

In the conventional surface plasmon resonance measurement apparatus employing the aforementioned system, the metal film on which a sample is placed must be exchanged each time a measurement is made. Because of this, the metal film is fixed on a first dielectric block in the form of a plate, and a second dielectric block in the form of a prism is provided as an optical coupler for making the aforementioned total internal reflection occur. The first dielectric block is integrated with a surface of the second dielectric block. The second dielectric block is fixed with respect to an optical system. The first dielectric block and the metal film are used as a measuring chip. In this manner, the measuring chip can be exchanged every time a measurement is made.

In addition, a leaky mode measurement apparatus is known as a similar measurement apparatus making use of ATR (for example, see "Spectral Research," Vol. 47, No.1 (1998), pp. 21 to 23 and pp. 26 to 27). This leaky mode measurement apparatus includes (1) a dielectric block formed into the shape of a prism; (2) a cladding layer formed on a surface of the dielectric block; (3) an optical waveguide layer, formed on the cladding layer, for placing a sample thereon; (4) a light source for emitting a light beam; (5) an optical system for making the light beam enter the dielectric block at various angles of incidence so that a condition for total internal reflection is satisfied at the interface between the dielectric block and the cladding layer; and (6) photodetection means for measuring the intensity of the light beam totally reflected from the interface to detect the excited state of a waveguide mode, i.e., the state of ATR.

In the above-described leaky mode measurement apparatus, if a light beam strikes the cladding layer through the dielectric block at incidence angles greater than a critical incidence angle at which total internal reflection (TIR) takes place, the light beam is transmitted through the cladding layer. Thereafter, in the optical waveguide layer formed on the cladding layer, only light with a specific wave number, incident at a specific incidence angle propagates in a waveguide mode. If the waveguide mode is excited in this manner, most of the incident light is confined within the optical waveguide layer, and consequently, ATR occurs in which the intensity of light totally reflected from the aforementioned interface drops sharply. The wave number of the light propagating through the optical waveguide layer depends upon the refractive index of the sample on the optical waveguide layer. Therefore, the refractive index of the liquid sample and the properties of the liquid sample related to the refractive index can be analyzed by finding the above-described specific incidence angle $\theta_{sp}$ at which ATR takes place.

In the leaky mode measurement apparatus, as with the aforementioned surface plasmon resonance measurement apparatus, a first dielectric block is fixed with respect to the optical system, and the cladding layer and the optical waveguide layer are formed on a second dielectric block and used as a measuring chip. When a sample is exchanged, only the measuring chip can be exchanged.

However, in the case where the conventional measuring chip which is exchangeable is employed, a gap occurs between the first dielectric block and the second dielectric block and the refractive index becomes discontinuous. To prevent the discontinuity, it is necessary that the two dielectric blocks be united through an index-matching solution. The operation of uniting the two dielectric blocks into an integral body is fairly difficult, and consequently, the conventional measuring chip is not easy to handle in making a measurement. There are cases where measurement is automated by automatically loading a plurality of measuring chips into a turret, then rotating the turret, and automatically supplying the measuring chips to a measuring position where a light beam enters the measuring chip. In such a case, the loading and removal of the measuring chips are time-consuming. As a result, the efficiency of the automatic measurement is reduced.

In addition, there is a possibility that the conventional measuring chip will have a detrimental influence on the environment, because it uses an index-matching solution.

In view of the circumstances mentioned above, there has been proposed a surface plasmon resonance measuring chip that can be easily exchanged without using an index-matching solution (see U.S. Patent Laid-Open No. 20010040680). The measuring chip comprises (1) a dielectric block; (2) a thin film layer, formed on a surface of the dielectric block, for placing a sample thereon; (3) a light source for emitting a light beam; (4) an optical system for making the light beam enter the dielectric block so that a condition for total internal reflection is satisfied at an interface between the dielectric block and the thin film layer and that the light beam has incident components at various angles; and (5) photodetection means for detecting the intensity of the light beam totally reflected from the interface to detect the state of ATR. The dielectric block is formed as a single block, which includes an entrance surface through which the light beam enters the dielectric block, an exit surface through which the light beam emerges from the dielectric block, and a surface on which the thin film layer is formed. The thin film layer is integrated with the dielectric block.

Note that in the case where the measuring chip is used in the above-described surface plasmon resonance measurement apparatus, the above-described thin film layer is constructed of a metal film. In the case where it is used in a leaky mode measurement apparatus, the thin film layer is constructed of a cladding layer and an optical waveguide layer. In addition, the dielectric block constituting the measuring chip preferably has a sample holder for holding a sample on the thin metal film, formed by surrounding the space above the thin metal film from the sides thereof.

The above-described dielectric block, incidentally, is generally injection-molded into the shape of a truncated quadrangular pyramid, a square pole, etc., and is suitably employed. However, in a conventional measuring chip equipped with such a resin dielectric block, there are cases where the reproducibility of measured data is not good.

SUMMARY OF THE INVENTION

The present invention has been made in view of the above-described circumstances. Accordingly, it is the primary object of the present invention to provide a measuring chip which is excellent in reproducibility of measured data.

To achieve this end and in accordance with the present invention, there is provided a first measuring chip comprising a dielectric block and a thin film layer formed on one surface of the dielectric block. The thin film layer is used for placing a sample thereon.

The measuring chip is employed in a measurement apparatus utilizing attenuated total reflection and comprising a light source for emitting a light beam, an optical system for making the light beam enter the dielectric block at various angles of incidence so that a condition for total internal reflection is satisfied at an interface between the dielectric block and the thin film layer, and photodetection means for measuring the intensity of the light beam totally reflected from the interface to detect attenuated total reflection.

The dielectric block is formed as a single block which includes an entrance surface at which the light beam enters the dielectric block, an exit surface from which the light beam emerges, and the one surface on which the thin film layer is formed. In addition, the dielectric block is integrated with the thin film layer and formed from a resin whose photoelastic coefficient is less than $50 \times 10^{-12}$ $Pa^{-1}$.

The above-described measuring chip includes a measuring chip for the aforementioned surface plasmon resonance measurement apparatus which employs a metal film as the above-described thin film layer, and a measuring chip for the aforementioned leaky mode measurement apparatus in which the above-described thin film layer comprises a cladding layer formed on one surface of a dielectric block, and an optical waveguide layer formed on the cladding layer.

In the measurement apparatus employing the measuring chip of the present invention, there are various methods of analyzing a sample by detecting the intensity of a light beam totally reflected from the aforementioned interface with photodetection means. For example, a light beam is caused to strike the aforementioned interface at various angles of incidence so that a total internal reflection condition is satisfied at the interface. Then, the intensity of the light beam totally reflected from the interface is measured at each position corresponding to each incidence angle. Next, by detecting the position (angle) of a dark line produced due to attenuated total reflection (ATR), a sample held by the measuring chip is analyzed.

In addition, a light beam with a plurality of wavelengths is caused to enter a measuring chip at angles of incidence so that a total internal reflection condition is satisfied at the interface. Then, the intensity of the light beam totally reflected from the interface is measured for each wavelength. Next, by measuring the degree of ATR for each wavelength, a sample held by the measuring chip is analyzed (see D. V. Noort, K. Johansen, C. -F. Mandenius, Porous Gold in Surface Plasmon Resonance Measurement, EUROSENSORS XIII, 1999, pp. 585–588).

Furthermore, a light beam is caused to enter a measuring chip at an angle of incidence so that a total internal reflection condition is satisfied at the aforementioned interface. Meanwhile, the light beam is split into two light beams before the light beam strikes the interface. One of the two light beams is caused to interfere with the other light beam totally reflected from the interface. Next, by measuring the intensity of the light beam after the interference, a sample held by the measuring chip is analyzed (see P. I. Nikitin, A. N. Grigorenko, A. A. Beloglazov, M. V. Valeiko, A. I. Savchuk, O. A. Savchuk, Surface Plasmon Resonance Interferometry for Micro-Array Biosensing, EUROSENSORS XIII, 1999, pp. 235–238).

Preferably, the photoelastic coefficient of the aforementioned resin is less than $20 \times 10^{-12}$ $Pa^{-1}$.

Figure 8:
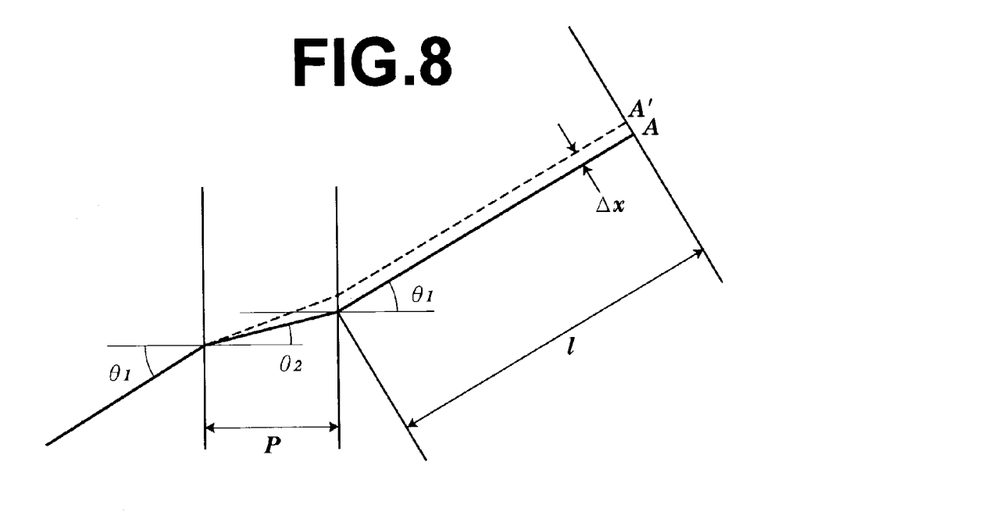
FIG. 8 is a diagram equivalently showing the optical path in a measurement apparatus employing the measuring chip of the present invention.

An optical path in a measurement apparatus employing the above-described measuring chip can be equivalently represented as shown in FIG. 8. Note in the figure that the interval P represents the optical path within the dielectric block of the measuring chip.

As shown in the figure, if the refractive index n of the dielectric block changes due to the water absorption of the dielectric body, the optical path changes from a solid line to a broken line, and a position detected by a sensor (photodetection means) moves from A(x) to A'($\Delta x+x$).

In the above-described surface plasmon resonance measurement apparatus or leaky mode measurement apparatus, such a fluctuation in the optical path due to a change in the refractive index n of the dielectric body is recognized in error as a fluctuation $\Delta\theta$ in the total reflection angle $\theta$ at the interface between the thin film layer and the dielectric block. When the width of the measuring chip is represented by P and the distance from the measuring chip to the sensor by l, the fluctuation $\Delta\theta$ in the total reflection angle $\theta$ is represented by Eq. (4), derived from the relationships of Eqs. (2) and (3).

$$l \cdot \tan(\theta 1 + \Delta\theta) = \Delta x + x \quad (2)$$

$$l \cdot \tan \theta 1 = x \quad (3)$$

$$\Delta\theta = \Delta x / l \cdot 180 / \pi \cdot \sin^2 \theta_1 \quad (4)$$

A fluctuation in the refractive index n of the dielectric body also causes $\theta 2$ to fluctuate. A fluctuation $\Delta\theta 2$ in the $\theta 2$ can be represented as Eq. (5). At this time, a fluctuation $\Delta x$ in the position can be represented as Eq. (6). From Eqs. (5) and (6), the positional fluctuation $\Delta x$ can be represented as Eq. (7).

$$\Delta\theta 2 = -180/\pi \cdot \Delta n/n \cdot \tan \theta 2 \quad (5)$$

$$\Delta x = P \cdot \pi \Delta\theta 2/180 \cdot 1/\sin^2 \theta 2 \quad (6)$$

$$\Delta x = P \cdot \Delta n/n \cdot 1/\cos \theta 2 \quad (7)$$

From Eqs. (4) and (7), the fluctuation $\Delta\theta$ in the total reflection angle $\theta$ can be represented as Eq. (8).

$$\Delta\theta = P/l \cdot \Delta n/n \cdot 1/\cos \theta 2 \cdot 180/\pi \cdot \sin^2 \theta \quad (8)$$

In Eq. (8), actual values in the measuring system are substituted for P, l, n, $\theta 1$, and $\theta 2$.

If $\theta 2 = 42°$ when P (width of the measuring chip)=5 mm, l (distance from the measuring chip to the sensor)=20 mm, n (refractive index of the dielectric body)=1.5, and $\theta_1$ (central incidence angle)=26°, an actual fluctuation $\Delta\theta$ in the measuring system is represented by Eq. (9).

$$\Delta\theta = 1.3 \cdot \Delta n \quad (9)$$

A diagram showing the relationship between the percentages of water absorption of typical resins (OZ-1000 and PMMA) and changes in the refractive index is shown in "Applications and Fabrication of Plastic Lens," CMC, p. 69.

Figure 9:
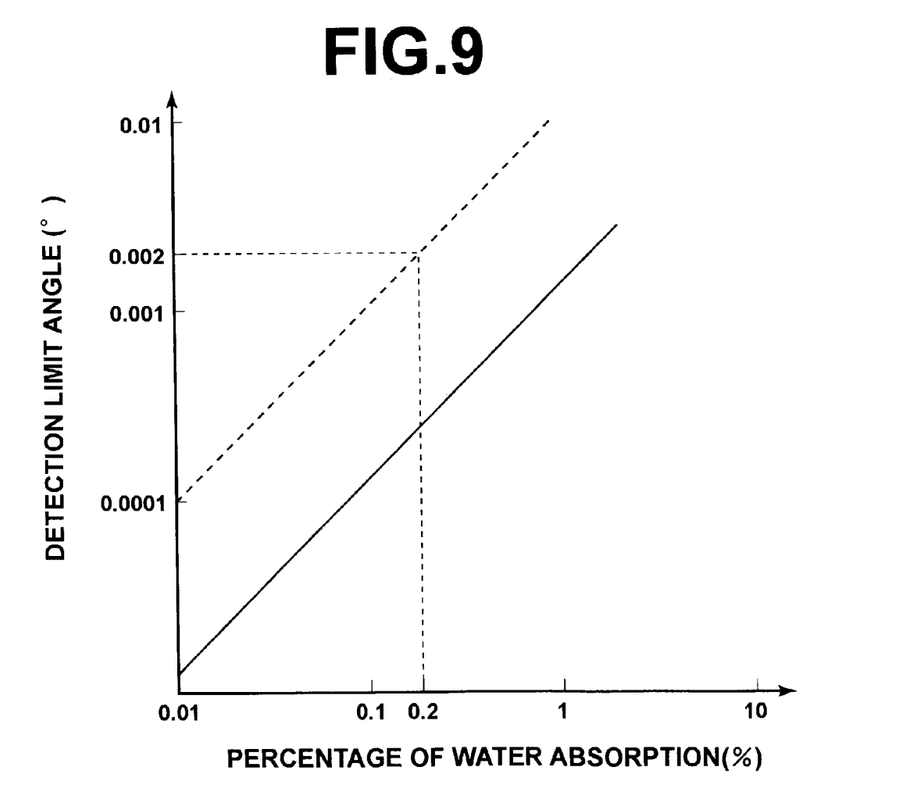
FIG. 9 is a graph showing the relationship between the percentage of water absorption of the dielectric block and the detection limit angle.

From the above-described diagram and Eq. (9), a signal fluctuation due to moisture absorption is obtained as shown in FIG. 9. In the figure, a solid line represents a signal fluctuation due to moisture absorption.

If measurements are made in a region where a signal fluctuation is about 1/10 or less, measured data can have a good S/N ratio without taking the influence of moisture absorption into consideration. The broken line in FIG. 9 represents the lower limit at which measurements can be made without taking the influence of moisture absorption into consideration.

Although a change in angle depends on the quantity of water absorption of a sample with respect to the thin film layer of the measuring chip, the detection limit angle equivalent to accuracy to the measurement of molecular weight 100 is approximately 0.001°.

In the field of pharmaceutical development, accuracy to the measurement of molecular weight 200, that is, a detection limit angle of 0.002°, is required. To meet this requirement, the percentage of water absorption of the dielectric block has to be less than 0.2%, as shown in FIG. 9.

For this reason, it is desirable to employ a resin whose percentage of water absorption is less than 0.2%. Note that the percentage of water absorption is based on a test method, ASTM D570. The percentages of water absorption described herein are all based on the ASTM D570. An example of such a resin is a cycloolefin polymer, and "ZEONEX 330R" (made by Nippon Zeon) is preferred.

When protein and a gene on the order of molecular weight 1000 (on the order of detection limit angle 0.01°) are measured, it is necessary that the percentage of water absorption of the dielectric block be less than 1%.

Investigations have been made with respect to the relationship between the surface area ratio of the metal film of a measuring chip for a surface plasmon resonance measurement apparatus and the sensitivity to measurement. The surface area ratio refers to a ratio $S_{ratio}$ of an actual surface area S to a surface area $S_o$ in the case where the metal film is assumed to be completely flat.

In the investigations, a cane sugar solution diluted to a concentration of 5/1000 and a cane sugar solution diluted to a concentration of 25/1000 were poured into the measuring chips equipped with metal films of surface area ratios 1.006 to 1.034, and measurements were made. A first signal was detected by measuring the cane sugar solution of the strength of 5/1000, and a second signal was detected by measuring the cane sugar solution of the strength of 25/1000. The difference between the first and second signals was obtained as sensitivity.

Figure 10:
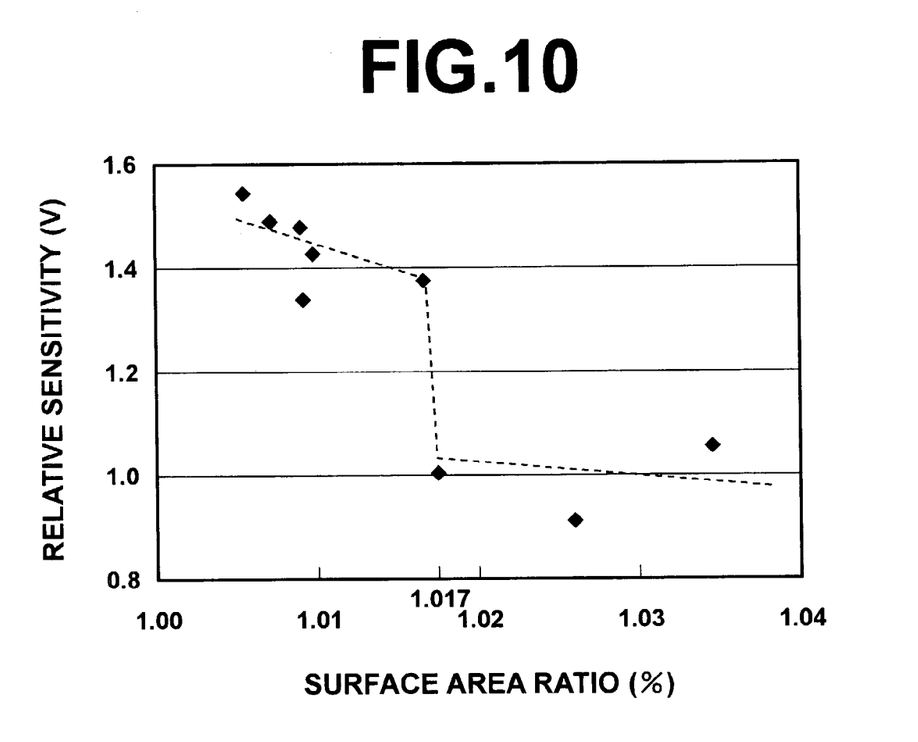
FIG. 10 is a graph showing the relationship between the surface area ratio of the metal film and the sensitivity to measurement.

In the measurement of the cane sugar solution, a light beam with a wavelength of 950 nm was irradiated to the measuring chips equipped with dielectric bodies made of "ZEONEX 330R." The dielectric bodies have 50-nm-thick Au films of surface area ratios 1.006 to 1.034. The results are shown in FIG. 10. In a graph shown in the figure, the axis of abscissas denotes a surface area rate and the axis of ordinates denotes relative sensitivity with the sensitivity at a surface area ratio of 1.017 as 1. It is understood from this graph that the sensitivity is about 1.4 times higher in the case where the surface area ratio is less than 1.017 than in the case where the surface area ratio is 1.017 or greater.

Therefore, in the case of a measuring chip for a surface plasmon resonance measurement apparatus in which the above-described thin film layer is employed as the metal film, it is preferable that the surface area ratio of the metal film be less than 1.017.

For example, in the case where the dielectric body is formed from "ZEONEX 330R" and the metal film comprises a 50-nm-thick Au film, vapor deposition is performed at a vacuum of $2.0 \times 10^{-6}$ or less and a film forming speed of 0.1 nm/s or greater so that the surface area ratio of the metal film is less than 1.017.

The inventors have made various investigations and experiments and found the following fact. That is, the cause of the reproducibility of measured data not being good in using a conventional measuring chip constructed of a resin dielectric block lies in that a resin whose photoelastic coefficient is relatively great is employed as the material of the dielectric block. More specifically, a resin dielectric block is formed, for example, by injection molding, etc. And because of mechanical strain produced when resin is cooled and hardened, double refraction tends to occur in the dielectric block.

In a measuring chip for surface plasmon resonance measurement, for example, measuring light is caused to strike the interface between the dielectric block and the thin film layer (metal film) in a state of p-polarization, but the p-polarized light component of the measuring light beam is increased or decreased according to double refraction produced in the dielectric block. Because of this, the quantity of total reflection will fluctuate independently of the dielectric constant of a sample to be measured. If the photoelastic coefficient of the material (resin) of the dielectric block is greater, then the above-described double refraction will become higher. Consequently, a fluctuation in the quantity of total reflection becomes greater and the value of measured data fluctuates.

On the other hand, in a measuring chip for leaky mode measurement, when linearly polarized light is not incident on the interface between the dielectric block and the thin film layer (cladding layer), there are cases where the S/N ratio of a signal totally reflected from the interface is reduced or the polarity of the signal is reversed. Therefore, if the double refraction occurring in the material (resin) of the dielectric block is high, then the state of linear polarization of the measuring light cannot be maintained until it reaches the interface, and consequently, the value of measured date will fluctuate.

Figure 6:
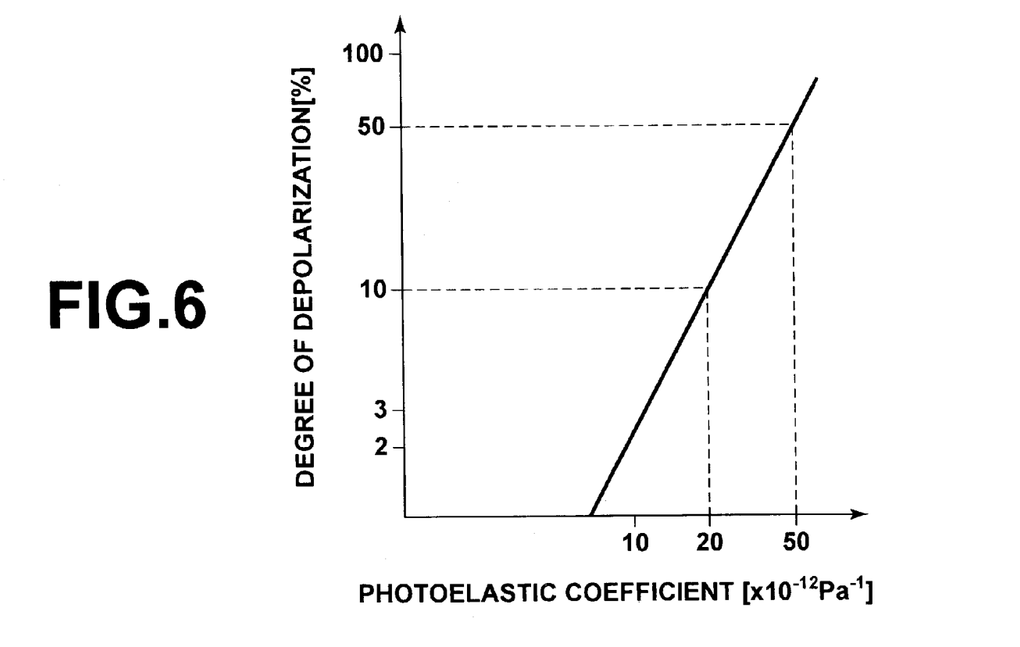
FIG. 6 is a graph showing the relationship between the photoelastic coefficient of the material of a dielectric block and the degree of depolarization of the linearly polarized light passed through the dielectric body.

The inventors have found that a fluctuation in measured data in the measuring chip for surface plasmon resonance measurement or leaky mode measurement is practically negligible if the state of polarization immediately before the measuring chip is kept about 50%, and is almost negligible if it is kept about 90% (i.e., if the degree of depolarization is about 10% or less). FIG. 6 shows the relationship between the photoelastic coefficient of the material (resin) of a dielectric block and the degree of depolarization of the linearly polarized light passed through the dielectric body. It can be seen from the figure that when the photoelastic coefficient is $50 \times 10^{-12}$ Pa$^{-1}$ and $20 \times 10^{-12}$ Pa$^{-1}$, the degree of depolarization is the above-described values, that is, 50% and 10%. Hence, in the present invention, the photoelastic coefficient of the material of the dielectric block is less than $50 \times 10^{-12}$ Pa$^{-1}$, preferably less than $20 \times 10^{-12}$ Pa$^{-1}$. Therefore, in the measuring chip of the present invention, the degree of depolarization of linearly polarized light can be reduced, and measured data with less fluctuation and good reproducibility can be obtained.

Figure 7:
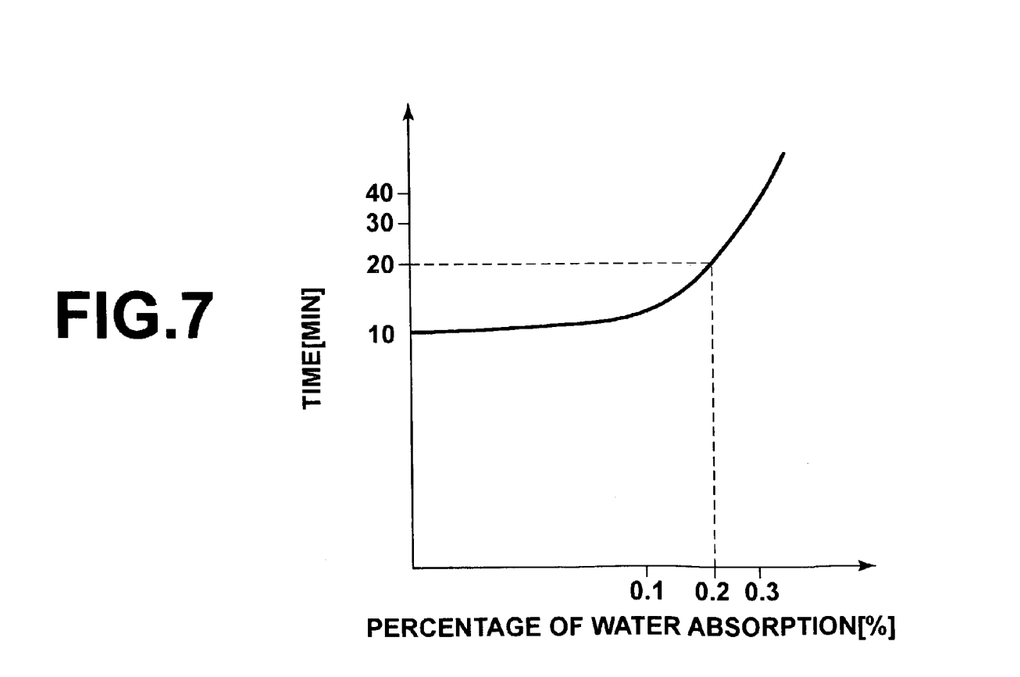
FIG. 7 is a graph showing the relationship between the percentage of water absorption of the material of a dielectric block and the deaerating time required in vapor-depositing a thin film layer on the dielectric block.

In the measuring chip of the present invention, the film layer (metal film, etc.,) that is formed on one surface of the dielectric block is usually formed by vapor deposition. If the percentage of water absorption of the dielectric body is higher when vapor deposition is performed, then the time required for deaerating the vapor deposition device up to a vacuum state will become longer. FIG. 7 is a graph showing the relationship between the percentage of water absorption of the material of a dielectric block and the deaerating time required in vapor-depositing a metal film on the dielectric block (time required to deaerate the vapor deposition device up to $4 \times 10^{-12}$ Pa$^{-1}$). As shown in the figure, if the percentage of water absorption is less than 0.2%, the above-described deaerating time is reduced to less than 20 min which is practically allowable in almost all cases, and the time required for vapor deposition can be shortened.

Note that if the percentage of the material (resin) of the dielectric block is great, the dielectric body will absorb the water in a sample during measurement and therefore the refractive index will change greatly. If the refractive index of the dielectric body changes greatly in this way, the angle at which attenuated total reflection (ATR) takes place will fluctuate regardless of the dielectric constant or refractive index of a sample to be measured. Therefore, if a resin whose percentage of water absorption is low is employed as the material of the dielectric body, a fluctuation in measured data due to the moisture absorption of the dielectric block can be reduced.

BRIEF DESCRIPTION OF THE DRAWINGS

The present invention will be described in further detail with reference to the accompanying drawings wherein.

DESCRIPTION OF THE PREFERRED EMBODIMENTS

Referring now in greater detail to the drawings and initially to FIG. 1, there is shown a surface plasmon resonance measurement apparatus which employs surface plasmon resonance measuring chips (hereinafter referred to simply as measuring chips) 10 constructed in accordance with a first embodiment of the present invention.

Figure 1:
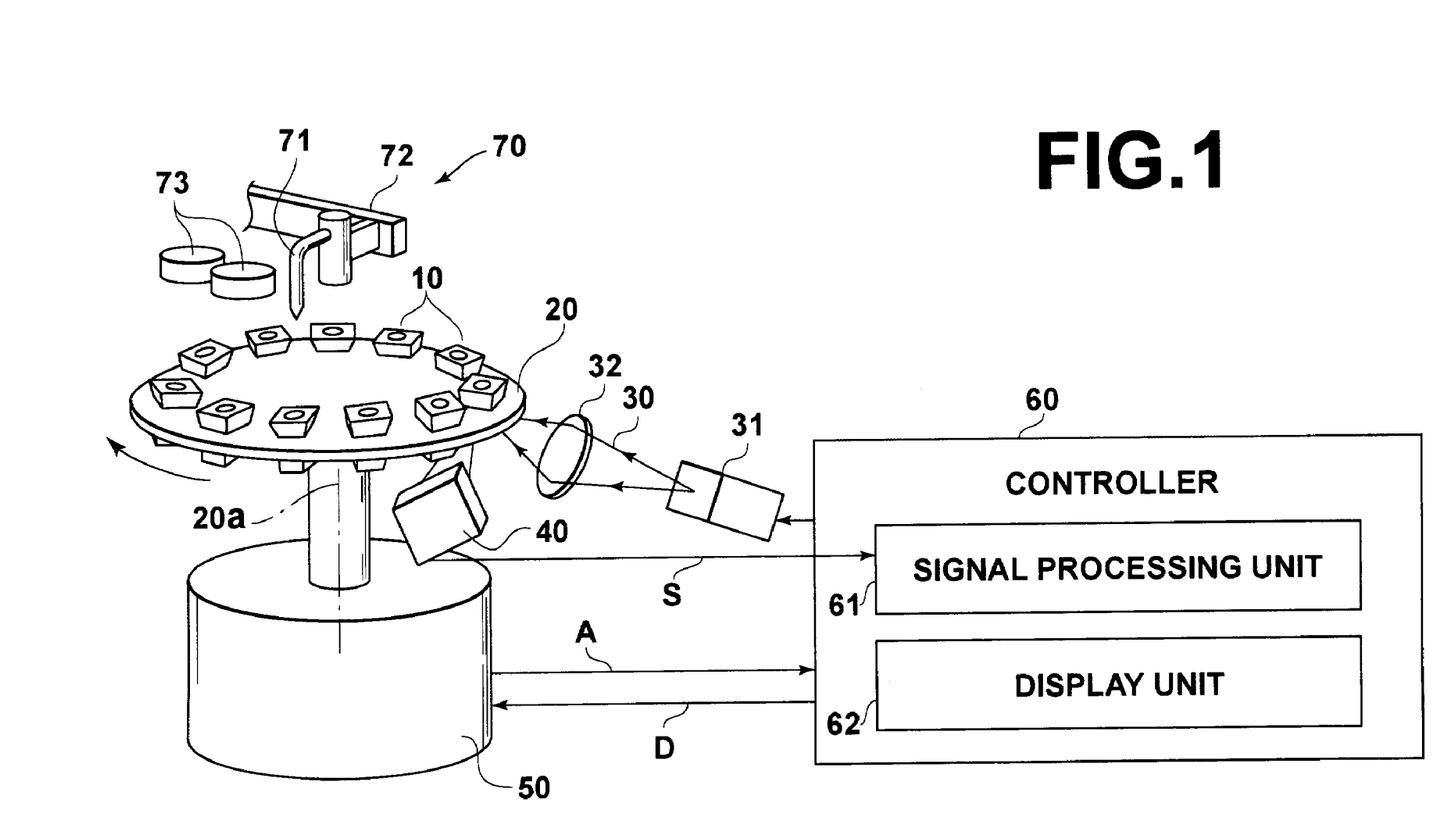
FIG. 1 is a perspective view showing a surface plasmon resonance measurement apparatus that employs surface plasmon resonance measuring chips constructed in accordance with a first embodiment of the present invention.

As illustrated in FIG. 1, the surface plasmon resonance measurement apparatus has a turntable 20 for supporting a plurality of measuring chips 10. The apparatus also has a laser light source (e.g., a semiconductor laser) 31 for emitting a measuring light beam (e.g., a laser beam) 30, a condenser lens 32 constituting an optical incidence system, and a photodetector 40. The apparatus further has supporting-body drive means 50 for rotating the turntable 20 intermittently, a controller 60, and an automatic sample supply mechanism 70. The controller 60 controls the supporting-body drive means 50, and also performs a process described later in response to a signal S from the photodetector 40.

Figure 2:
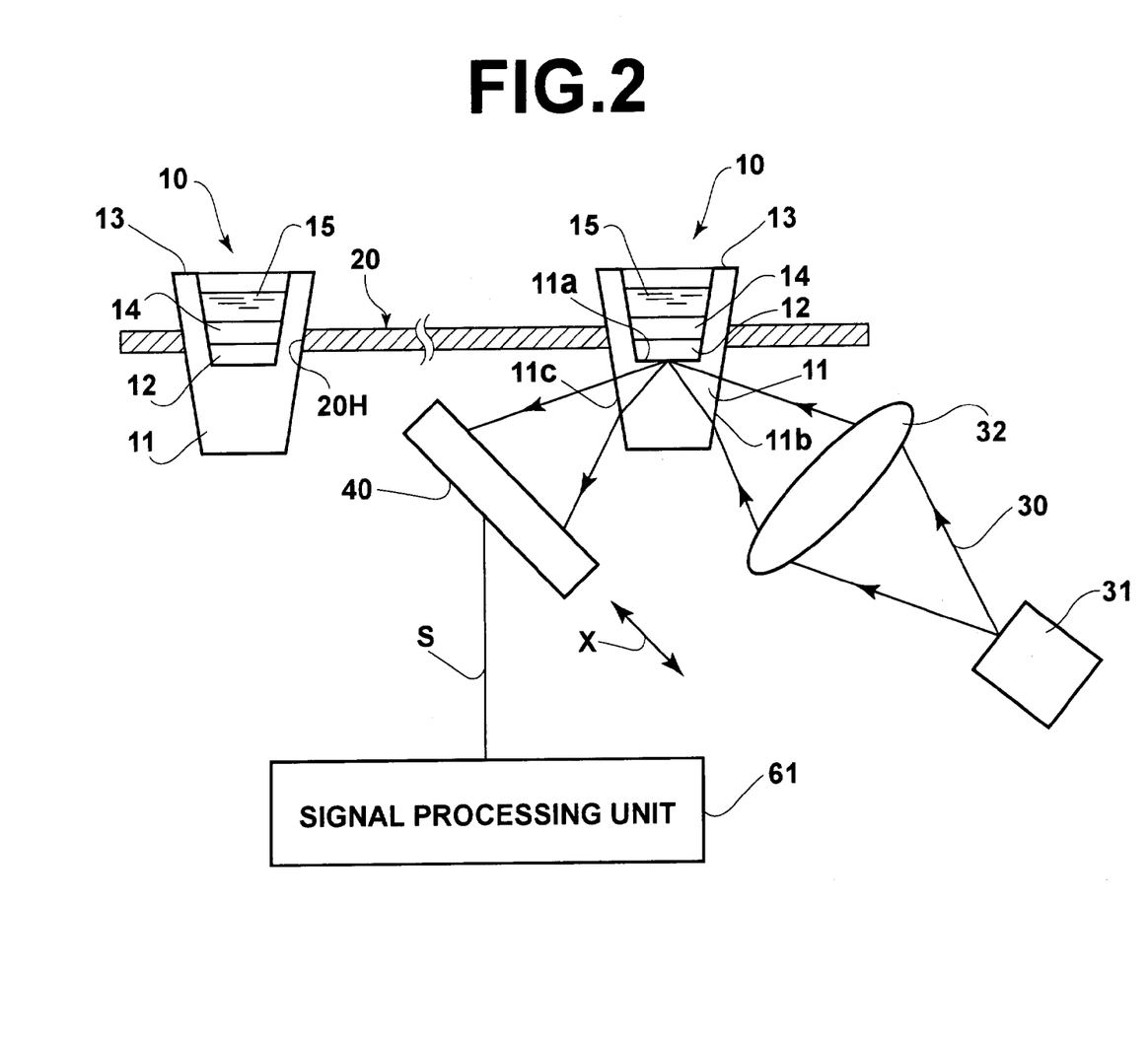
FIG. 2 is a part-sectional side view showing the surface plasmon resonance measurement apparatus of FIG. 1.
Figure 3:
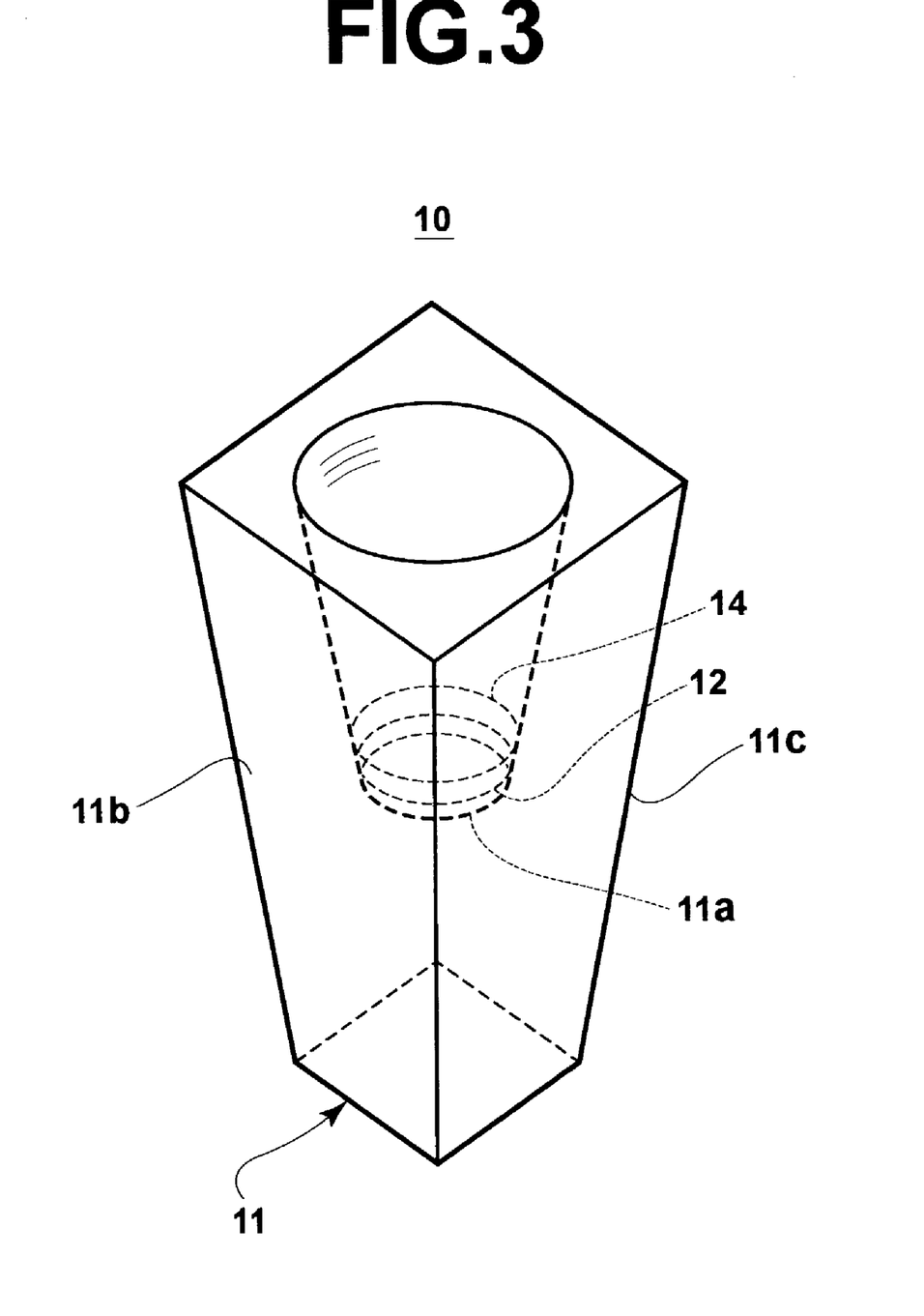
FIG. 3 is a perspective view of the surface plasmon resonance measuring chip shown in FIG. 1.

The measuring chip 10, as shown in FIGS. 2 and 3, is constructed of a transparent dielectric block 11, a metal film 12, and a sample holder 13. The dielectric block 11 is formed, for example, into the shape of a truncated quadrangular pyramid. The metal film 12 is formed on the top surface of the dielectric block 11 and made of gold, silver, copper, aluminum, etc. The sample holder 13 is formed on the dielectric block 11 and has a cylindrical portion for holding a sample on the metal film 12. The dielectric block 11 is formed as a single block, which includes a top surface 11a (interface to be described later) on which the metal film 12 is formed; an entrance surface 11b through which the light beam 30 enters; and an exit surface 11c from which the light beam 30 emerges. The sample holder 13 holds a liquid sample 15, as described later.

The dielectric block 11 and the sample holder 13, which constitute the measuring chip 10, are integrally formed from a transparent resin. The measuring chip 10 is exchangeable with respect to the turntable 20. That is, the measuring chip 10 is detachably fitted in a corresponding hole formed in the turntable 20 so that it can be exchanged.

In the first embodiment, the transparent resin of the dielectric block 11 employs ZEONEX 330R (made by Nippon Zeon). The ZEONEX 330R is a cycloolefin polymer, and the properties thereof are to be described later. In the first embodiment, a sensing medium 14 is fixed on the metal film 12 for reasons to be described later. The refractive index of the resin material of the dielectric block 11 is preferably in a range of about 1.45 to 2.5. The reason is that practical surface plasmon resonance (SPR) angles are obtained in the aforementioned refractive index range.

The turntable 20 is constructed such that a plurality of measuring chips 10 is supported at equiangular intervals on a circle with respect to the rotation axis 20a. In the first embodiment, 11 (eleven) measuring chips 10 are employed. The supporting-body drive means 50 is constructed of a stepping motor, etc., and is rotated intermittently at equiangular intervals equal to the pitch between the measuring chips 10.

The condenser lens 32, as shown in FIG. 2, is used to collect the light beam 30 emitted from the light source 31. The collected light beam 30 enters the dielectric block 11 at the entrance surface 11b and converges at the interface 11a between the dielectric block 11 and the metal film 12 so that various angles of incidence are obtained. That is, in the incidence angle range, a total internal reflection (TIR) condition for the light beam 30 is satisfied at the interface 11a, and surface plasmon resonance (SPR) is able to take place. Note that for convenience, the interface between the dielectric block 11 and the metal film 12 is represented by the same reference numeral 11a as the top surface 11a of the dielectric block 11.

Notice that the light beam 30 is caused strike the interface 11a as p-polarized light. For this reason, it is necessary to dispose the laser light source 31 so that the polarization direction thereof becomes a predetermined direction. Alternatively, the polarization direction of the light beam 30 may be controlled with a wavelength plate, a polarizing plate, etc.

The photodetector 40 is constructed of a line sensor in which a great number of light-receiving elements are arrayed in a row and along the direction of arrow X in FIG. 2.

The controller 60 receives an address signal A representing a position where rotation of the supporting-body drive means 50 is stopped, from the supporting-body drive means 50. This controller 60 also outputs a drive signal D to actuate the supporting-body drive means 50, based on a predetermined sequence. The controller 60 includes a signal processing unit 60 to which the output signal S from the photodetector 40 is input, and a display unit 62 to which a signal from the signal processing unit 61 is output.

The automatic sample supply mechanism 70 is constructed of a pipette 71 for suctioning and holding a predetermined quantity of a liquid sample, and means 72 for moving the pipette 71. The automatic sample supply mechanism 70 suctions and holds a liquid sample from a sample container 73 through the pipette 71, and supplies the liquid sample to the sample holder 13 of the measuring chip 10 being stopped at a predetermined position.

A description will hereinafter be given of how a sample is analyzed by the surface plasmon resonance measurement apparatus constructed as described above. The turntable 20 is rotated intermittently by the supporting-body drive means 50, as previously mentioned. When the turntable 20 is stopped, a sample 15 is supplied by the automatic sample supply mechanism 70 to the sample holder 13 of the measuring chip 10 being stopped at a predetermined position.

If the turntable 20 is further rotated a few times and stopped, the measuring chip 10 with the sample 15 in the sample holder 13 is located at a measuring position (see FIG. 2) where the light beam 30 enters the dielectric block 11. When the measuring chip 10 is held in the measuring position, the laser light source 31 is driven in response to a command from the controller 60. The light beam 30 emitted from the laser light source 31 is collected by the condenser lens 32 and strikes the interface 11a between the dielectric block 11 and the metal film 12 in a state of convergence. The light beam 30 totally reflected from the interface 11a is detected by the photodetector 40.

The light beam 30 has components that are incident on the interface 11a at various incidence angles $\theta$, because it enters the dielectric block 11 in a state of convergence, as mentioned above. Note that these incidence angles $\theta$ are equal to or greater than a critical angle at which total internal reflection (TIR) takes place. Therefore, the light beam 30 is totally reflected from the interface 11a, and has components that are reflected at various angles of reflection. The optical system, which includes the condenser lens 32, etc., may be constructed so that the light beam 30 strikes the interface 11a in a defocused state. In such a case, errors in the measurement of surface plasmon resonance (e.g., errors in the measurement of the position of the dark line) are averaged and therefore accuracy of measurement is enhanced.

Figure 4:
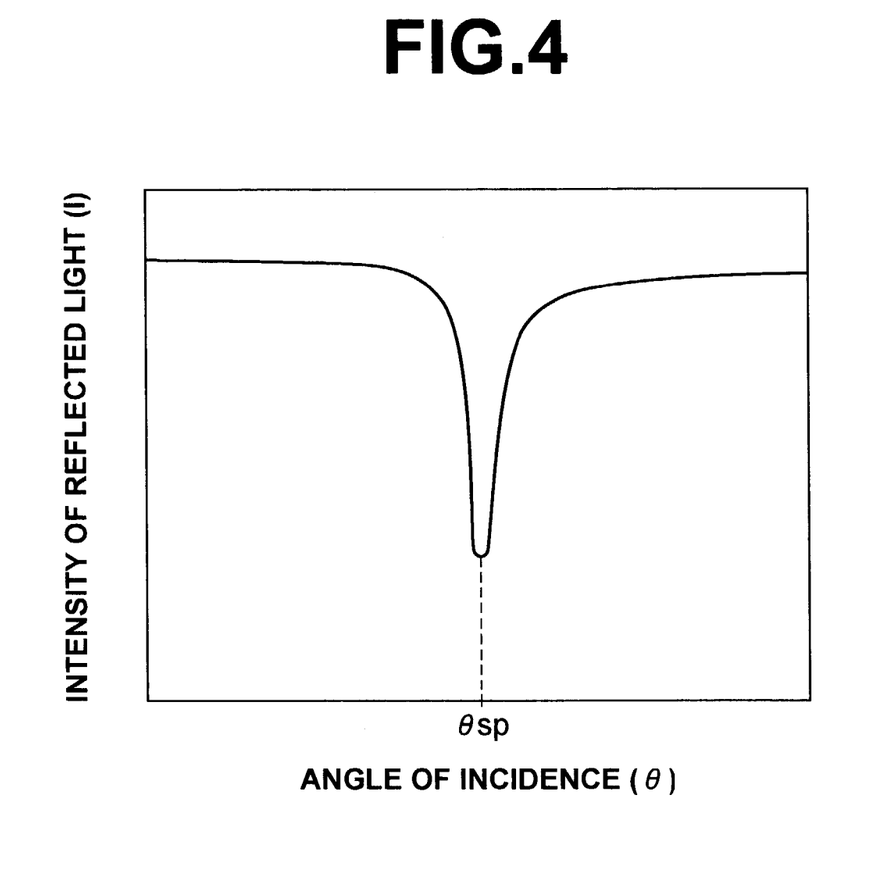
FIG. 4 is a graph showing the relationship between the incidence angle at which a light beam enters the measuring chip, and the intensity of the light beam reflected from the measuring chip.

When the light beam 30 satisfies total internal reflection at the interface 11a, as described above, an evanescent wave propagates on the side of the metal film 12 through the interface 11a. And when the light beam 30 strikes the interface 11a at a specific incidence angle $\theta_{sp}$, the evanescent wave resonates with the surface plasmon excited on the surface of the metal film 12. Because of this, the intensity I of the reflected light drops sharply. The relationship between the specific incidence angle $\theta_{sp}$ and the light intensity I is shown in FIG. 4.

Hence, the quantity of light detected by each light-receiving element is calculated from the light-quantity detection signal S output from the photodetector 40. Based on the calculated light quantity (i.e., based on the position of the light-receiving element that detected a dark line), the specific incidence angle $\theta_{sp}$ (at which ATR occurs) is obtained. Therefore, according to previously obtained curves which represent the relationship between the reflected-light intensity I and the specific incidence angle $\theta_{sp}$, a specific substance in the sample 15 can be quantitatively analyzed. The signal processing unit 61 of the controller 60 quantitatively analyzes a specific substance in the sample 15, based on the above-described principle. The result of analysis is displayed on the display unit 62.

In the case where a single measurement is made on a single sample 15, the measurement is completed in the manner described above. Therefore, in this case, the measuring chip 10 on which a measurement was made is removed from the turntable 20 by hand or with automatic removal means. On the other hand, in the case where a plurality of measurements are made on a single sample 15, each of the measuring chips 10 is still supported by the turntable 20 after the first measurement. After one revolution of the turntable 20, the sample 15 held in each of the measuring chips 10 can be measured again.

In the surface plasmon resonance measurement apparatus as described above, a plurality of measuring chips 10 are supported by the turntable 20 and are sequentially located at the measuring position by rotating the turntable 20. Therefore, the samples 15 held in the sample holder 13 of the measuring chips 10 can be successively measured by movements of the turntable 20. Thus, the surface plasmon resonance measurement apparatus of the first embodiment is capable of measuring a great number of samples 15 in a short time.

In the measuring chip 10 according to the first embodiment, the optical coupling of the dielectric block 11 with another dielectric block through an index-matching solution is not needed as is done in prior art. Thus, the measuring chip 10 of the first embodiment is easy to handle and does not require an index-matching solution that would have a bad influence on the environment.

Note that the sensing medium 14 fixed on the surface of the metal film 12 is bound to a specific substance in the sample 15. An example of a combination of a specific substance in the sample 15 and the sensing medium 14 is a combination of an antigen and an antibody. In that case, an antigen-antibody reaction can be detected, based on the specific angle $\theta_{sp}$ at which attenuated total reflection (ATR) takes place.

Now, the measuring chip 10 will be described in detail. In the first embodiment, the dielectric block 11 constituting the measuring chip 10 is injection-molded by employing the "ZEONEX 330R" (Nippon Zeon) which is a cycloolefin polymer.

The photoelastic coefficient of the "ZEONEX 330R" is $6.5 \times 10^{-12}$ $Pa^{-1}$, which is smaller than the aforementioned $50 \times 10^{-12}$ $Pa^{-1}$ and $20 \times 10^{-12}$ $Pa^{-1}$. Thus, the dielectric body 11 is formed from a resin whose photoelastic coefficient is extremely small. Therefore, the measuring chip 10 of the first embodiment is excellent in reproducibility of measured data for the reasons described above.

To measure the aforementioned photoelastic coefficient, a test piece of 130 mm in length, 15 mm in width, and 5 mm in thickness was made. The test piece was placed on the sample stage of an automatic polarization analyzer (e.g., ellipsometer AEP=100 (Shimadzu)), and double refraction was measured at certain points with a load applied to the test piece. The relationship between the load and the double refraction was found and the photoelastic coefficient was calculated from the slope of a straight line representing the relationship.

On the other hand, the percentage of water absorption of the aforementioned "ZEONEX 330R" is less than 0.01%, which is smaller than the aforementioned 0.2%. Note that the value of this percentage of water absorption was obtained by the above-described ASTM D570 test method.

Thus, the electric block 11 is formed from a resin whose percentage of water absorption is extremely small. Therefore, the deaerating time in vapor-depositing the metal film 12 on the dielectric block 11 can be shortened. In addition, a great fluctuation in the measured data by a change in the refractive index due to the moisture absorption of the dielectric body 11 can be prevented. Furthermore, if the surface area ratio of the metal film 12 is made less than 1.017, sensitivity to measurement can be enhanced for the reasons described above.

Figure 5:
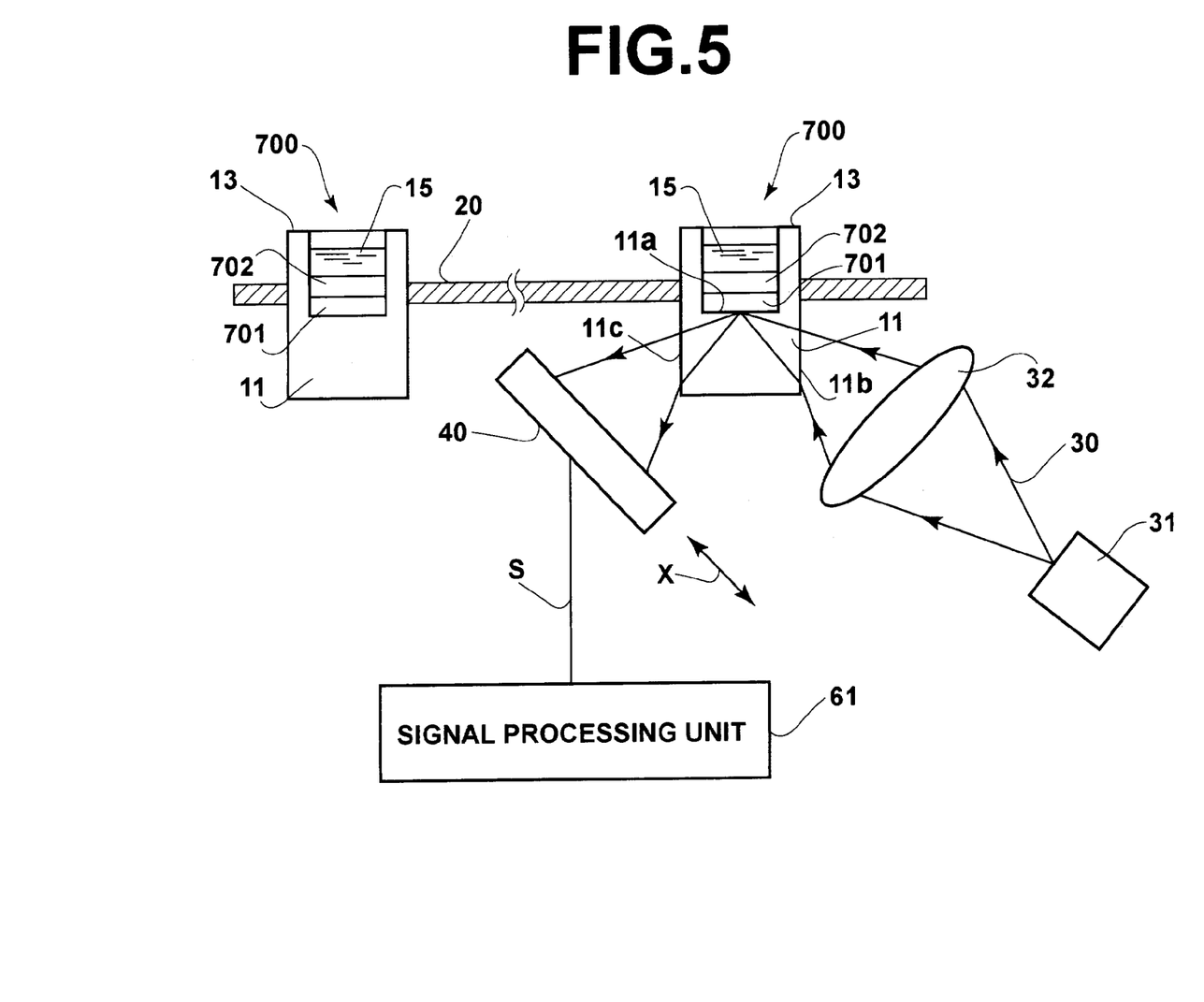
FIG. 5 is a part-sectional view of a leaky mode measurement apparatus which employs surface plasmon resonance measuring chips constructed in accordance with a second embodiment of the present invention.

Referring now to FIG. 5, there is shown a leaky mode measurement apparatus that employs measuring chips 700 constructed in accordance with a second embodiment of the present invention. The leaky mode measurement apparatus is basically the same in construction as the surface plasmon resonance measurement apparatus shown in FIG. 2. The measuring chip 700 includes a cladding layer 701 formed on one surface (e.g., the top surface) of a dielectric body 11, and an optical waveguide layer 702 formed on the cladding layer 701.

The dielectric block 11 is injection-molded by employing, for example, the aforementioned resin, "ZEONEX 330R." The cladding layer 701 is formed into the shape of a thin film by employing a dielectric or metal (such as gold, etc.) lower in refractive index than the dielectric block 11. The optical waveguide layer 702 is also formed into a thin film by employing a dielectric which is higher in refractive index than the cladding layer 701. The film thickness of the cladding layer 701 is 36.5 nm in the case where it is formed from a thin gold film. The film thickness of the optical waveguide layer 72 is about 700 nm in the case where it is formed from polymethylmethacrylate (PMMA).

In the leaky mode measurement apparatus, if a light beam 30 emitted from a laser light source 31 strikes the cladding layer 701 through the dielectric block 11 at incidence angles greater than a critical angle at which total internal reflection (TIR) occurs, the light beam 30 is totally reflected from the interface 11a between the dielectric block 11 and the cladding layer 701. However, the light with a specific wave number, incident on the optical waveguide layer 702 through the cladding layer 701 at a specific incidence angle, propagates through the optical waveguide layer 702 in a waveguide mode. If the waveguide mode is excited in this manner, most of the incident light is confined within the optical waveguide layer 702, and consequently, ATR occurs in which the intensity of the light totally reflected from the interface 11a drops sharply.

The wave number of the light propagating through the optical waveguide layer 702 depends upon the refractive index of the sample 15 on the optical waveguide layer 702. Therefore, the refractive index of the sample 15 and the properties of the sample 15 related to the refractive index can be measured by finding the above-described specific incidence angle $\theta_{sp}$ at which ATR takes place. A signal processing unit 61 quantitatively analyzes a specific substance in the sample 15, based on the above-described principle. The result of analysis is displayed on a display unit (not shown).

In the measuring chip 700 of the second embodiment, the dielectric block 11 is likewise injection-molded by employing the aforementioned resin "ZEONEX 330R" in which the photoelastic coefficient is extremely small ($6.5 \times 10^{-12}$ $Pa^{-1}$) and the percentage of water absorption is extremely small (less than 0.1%). Therefore, the measuring chip 700 of the second embodiment is capable of exhibiting the same advantages as the measuring chip 10 of the first embodiment.

While the present invention has been described with reference to the preferred embodiments thereof, the invention is not to be limited to the details given herein, but may be modified within the scope of the invention hereinafter claimed.

What is claimed is:

1. A measuring chip comprising:
 a dielectric block; and
 a thin film layer, formed on one surface of said dielectric block, for placing a sample thereon;
 wherein said measuring chip is employed in a measurement apparatus utilizing attenuated total reflection and comprising
 a light source for emitting a light beam,
 an optical system for making said light beam enter said dielectric block at various angles of incidence so that a condition for total internal reflection is satisfied at an interface between said dielectric block and said thin film layer, and
 photodetection means for measuring the intensity of said light beam totally reflected from said interface to detect attenuated total reflection;
 wherein said dielectric block is formed as a single block which includes an entrance surface at which said light beam enters said dielectric block, an exit surface from which said light beam emerges, and said one surface on which said thin film layer is formed; and
 wherein said dielectric block is integrated with said thin film layer and formed from a resin whose photoelastic coefficient is less than $50 \times 10^{-12}$ $Pa^{-1}$,
 wherein said thin film layer comprises a metal film whose surface area ratio is less than 1.017,
 wherein the surface area ratio is a ratio $S_{ratio}$ of an actual surface area $S$ to a surface area $S_o$ in the case where the metal film is assumed to be completely flat.

2. The measuring chip as set forth in claim 1, wherein the photoelastic coefficient of said resin is less than $20 \times 10^{-12}$ $Pa^{-1}$.

3. The measuring chip as set forth in claim 1, wherein the percentage of water absorption of said resin based on ASTM D570 is less than 0.2%.

4. The measuring chip as set forth in claim 2, wherein the percentage of water absorption of said resin based on ASTM D570 is less than 0.2%.

5. The measuring chip as set forth in claim 1, wherein the percentage of water absorption of said resin based on ASTM D570 is less than 1%.

6. The measuring chip as set forth in claim 2, wherein the percentage of water absorption of said resin based on ASTM D570 is less than 1%.

* * * * *